US010039517B2

(12) United States Patent
Choi et al.

(10) Patent No.: US 10,039,517 B2
(45) Date of Patent: Aug. 7, 2018

(54) X-RAY IMAGING APPARATUS AND CONTROL METHOD THEREOF

(71) Applicants: SAMSUNG ELECTRONICS CO., LTD., Suwon-si (KR); Korea Advanced Institute of Science and Technology, Daejeon (KR)

(72) Inventors: Ji Young Choi, Suwon-si (KR); Jong Ha Lee, Hwaseong-si (KR); Young Hun Sung, Hwaseong-si (KR); Yunjeong Lee, Daejeon (KR); Seungryong Cho, Daejeon (KR)

(73) Assignees: SAMSUNG ELECTRONICS CO., LTD., Suwon-si (KR); Korea Advanced Institute Of Science and Technology, Daejeon (KR)

( * ) Notice: Subject to any disclaimer, the term of this patent is extended or adjusted under 35 U.S.C. 154(b) by 193 days.

(21) Appl. No.: 14/498,498

(22) Filed: Sep. 26, 2014

(65) Prior Publication Data
US 2015/0085972 A1  Mar. 26, 2015

(30) Foreign Application Priority Data
Sep. 26, 2013 (KR) .................. 10-2013-0114450

(51) Int. Cl.
A61B 6/00 (2006.01)
A61B 6/03 (2006.01)
(Continued)

(52) U.S. Cl.
CPC .............. *A61B 6/541* (2013.01); *A61B 6/032* (2013.01); *A61B 6/486* (2013.01); *A61B 6/503* (2013.01);
(Continued)

(58) Field of Classification Search
CPC ......... A61B 6/032; A61B 6/541; A61B 6/503; A61B 6/542; A61B 6/5205; A61B 6/545
See application file for complete search history.

(56) References Cited

U.S. PATENT DOCUMENTS 6,865,248 B1    3/2005 Rasche et al.
2008/0049890 A1  2/2008 Hsieh et al.
(Continued)

FOREIGN PATENT DOCUMENTS

JP  2013-059695 A    4/2013
KR  10-2006-0128707 A  12/2006
KR  10-1255224 B1    4/2013

*Primary Examiner* — Hoon Song
(74) *Attorney, Agent, or Firm* — Sughrue Mion, PLLC

(57) ABSTRACT

An X-ray imaging apparatus includes an X-ray generator configured to transmit X-rays to an object, an X-ray detector configured to detect the X-rays transmitted through the object and convert the detected X-rays into electrical signals, a gantry in which the X-ray generator and the X-ray detector are installed so as to be opposite to each other, the gantry being rotatable about a bore, a controller configured to control a rotation of the gantry during bio-signal cycles of the object so that the gantry is rotated from different start positions whenever one of the bio-signal cycles is started, and an image processor configured to generate a 4D image of the object by applying a prior image-based compressed sensing image reconstruction algorithm to plural 2D projection images acquired from the electrical signals generated by converting the X-rays detected during the rotation of the gantry.

11 Claims, 17 Drawing Sheets

(51) Int. Cl.
    *G06T 15/00*     (2011.01)
    *G06T 11/00*     (2006.01)
(52) U.S. Cl.
    CPC .......... *A61B 6/5229* (2013.01); *A61B 6/5288* (2013.01); *A61B 6/542* (2013.01); *G06T 11/006* (2013.01); *G06T 15/00* (2013.01); *A61B 6/4447* (2013.01); *G06T 2211/412* (2013.01); *G06T 2211/424* (2013.01)

(56) References Cited

U.S. PATENT DOCUMENTS

| | | |
|---|---|---|
| 2008/0101532 A1 | 5/2008 | Tkaczyk et al. |
| 2009/0161933 A1 | 6/2009 | Chen |
| 2011/0062354 A1* | 3/2011 | Pettinato ................ A61B 6/035 250/522.1 |
| 2013/0303884 A1* | 11/2013 | Kuntz .................. G06T 11/006 600/417 |

* cited by examiner

FIRST CARDIAC CYCLE

SECOND CARDIAC CYCLE

US 10,039,517 B2

X-RAY IMAGING APPARATUS AND CONTROL METHOD THEREOF

CROSS-REFERENCE TO RELATED APPLICATION

This application claims the benefit of Korean Patent Application No. 10-2013-0114450, filed on Sep. 26, 2013 in the Korean Intellectual Property Office, the disclosure of which is incorporated herein by reference.

BACKGROUND

1. Field

Exemplary embodiments relate to an X-ray imaging apparatus and a control method thereof which may improve the quality of a 4D image of a moving object, such as the heart, and reduce a radiation dose applied to a patient or medical staff.

2. Description of the Related Art

In general, an X-ray imaging apparatus acquires images of the inside of an object, such as a human body or an article, by applying X-rays to the object. The X-ray imaging apparatus easily detects the internal structure of the object, and is thus used to detect abnormalities, such as lesions at the inside of a human body, in medicine, or to detect the internal structure of an article or a machine part. Further, the X-ray imaging apparatus may be used to check the inside of baggage in an airport.

As X-ray imaging apparatuses, there are a digital radiography (DR) apparatus, a computed tomography (CT) apparatus, a full field digital mammography (FFDM) apparatus, etc.

Now, the operating principle of an X-ray imaging apparatus will be described. The X-ray imaging apparatus applies X-rays to an object, such as a human body or an article, and then receives X-rays which are transmitted through the object or X-rays which are not transmitted through the object and directly reach the X-ray imaging apparatus. The X-ray imaging apparatus converts the received X-rays into electrical signals, and reads out the converted electrical signals, thus generating X-ray images. The generated X-ray images are displayed through a display unit. Thereby, a user may detect the internal structure of the object.

SUMMARY

Therefore, it is an aspect of the exemplary embodiments to provide an X-ray imaging apparatus and a control method thereof which may improve the quality of a 4D image of a moving object, such as the heart, and reduce a radiation dose applied to a patient or medical staff.

Additional aspects of the exemplary embodiments will be set forth in part in the description which follows and, in part, will be obvious from the description, or may be learned by practice of the exemplary embodiments.

In accordance with an aspect of an exemplary embodiment, an X-ray imaging apparatus includes an X-ray generator configured to transmit X-rays to an object, an X-ray detector configured to detect the X-rays transmitted through the object and convert the detected X-rays into electrical signals, a gantry in which the X-ray generator and the X-ray detector are installed so as to be opposite to each other, the gantry being rotatable about a bore, a controller configured to control a rotation of the gantry during bio-signal cycles of the object so that the gantry is rotated from different start positions whenever one of the bio-signal cycles is started, and an image processor configured to generate a 4D image of the object by applying a prior image-based compressed sensing image reconstruction algorithm to a plurality of 2D projection images acquired from the electrical signals generated by converting the X-rays detected during the rotation of the gantry.

In accordance with a further aspect of an exemplary embodiment, a control method of an X-ray imaging apparatus includes controlling a rotation of a gantry, in which an X-ray generator and an X-ray detector are provided so as to be opposite to each other, during bio-signal cycles of an object so that the gantry is rotated from different start positions whenever the bio-signal cycles are started, and generating a 4D image of the object by applying a prior image-based compressed sensing image reconstruction algorithm to a plurality of 2D projection images of the object acquired during the rotation of the gantry.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
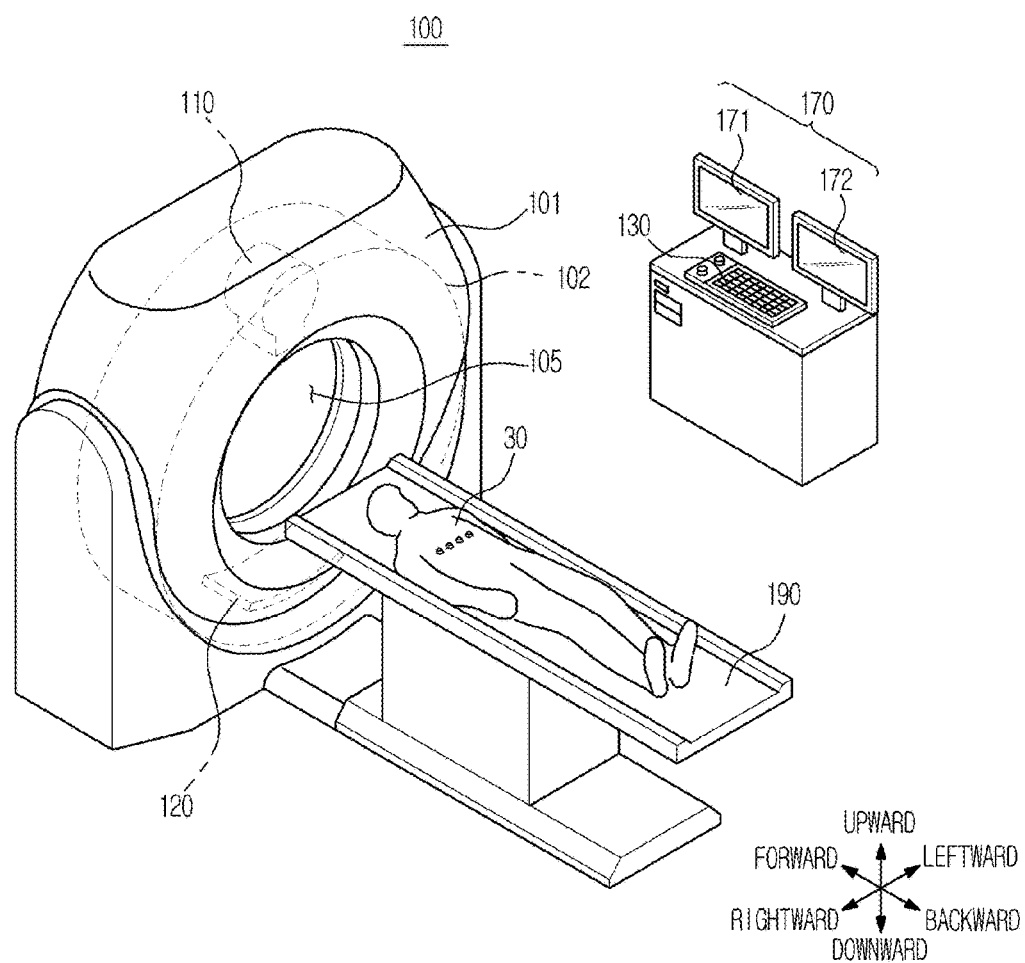
FIG. 1 is a perspective view of an X-ray imaging apparatus in accordance with an exemplary embodiment.

Reference will now be made in detail to the exemplary embodiments, examples of which are illustrated in the accompanying drawings, wherein like reference numerals refer to like elements throughout.

As X-ray imaging apparatuses, there are a digital radiography (DR) apparatus, a computed tomography (CT) apparatus, and a full field digital mammography (FFDM) apparatus. Hereinafter, a computed tomography (CT) apparatus may be exemplarily described as an X-ray imaging apparatus.

FIG. 1 is a perspective view of an X-ray imaging apparatus in accordance with an exemplary embodiment.

As exemplarily shown in FIG. 1, the X-ray imaging apparatus 100 may include a table 190, a housing 101, an input unit 130, and a display unit 170.

A gantry 102 may be mounted within the housing 101. An X-ray generator 110 and an X-ray detector 120 are mounted within the gantry 102 so as to be opposite to each other. The gantry 102 may be rotated by an angle of 180 to 360 degrees around a bore 105. As the gantry 102 is rotated, the X-ray generator 110 and the X-ray detector 120 are rotated. A position where the gantry 102 starts to rotate may be determined in advance. A time when the gantry starts to rotate may be determined based on a bio-signal of an object 30. For example, the bio-signal of the object 30 may be an electrocardiogram (ECG or EKG). Rotation methods of the gantry 102 will be described later with reference to FIGS. 2A and 2B.

The object 30 may be placed on the table 190 under the condition that at least one electrode to measure the ECG of the object 30 is attached to the object 30.

The table 190 transfers the object 30, which is a target of X-ray imaging, to the inside of the bore 105. The table 190 may be moved in the forward, backward, leftward, rightward, upward, and downward directions while being kept horizontally with the ground surface. As one example, after the position or height of the table 190 is adjusted in the leftward and rightward directions or in the upward and downward directions so that the center of the object 30 coincides with the center $C_{bore}$ of the bore 105, the table 190 may be moved to the inside of the bore 105. As another example, after the table 190 is moved to the inside of the bore 105, the position or height of the table 190 may be adjusted in the leftward and rightward directions or in the upward and downward directions so that the center of the object 30 coincides with the center $C_{bore}$ of the bore 105.

The input unit 130 may receive instructions or a command to control operation of the X-ray imaging apparatus 100. For this purpose, the input unit 131 may include at least one of a keyboard, a mouse and a foot pedal.

The display unit 170 may display X-ray images of the object 30. For example, the X-ray images may be 2D projection images acquired by applying X-rays to the object 30 and detecting X-rays transmitted through the object 30, 3D images, volumes of which are reconstructed from a plurality of 2D projection images, and a 4D image in which 3D images are arranged according to time.

The display unit 170 may include at least one display. FIG. 1 illustrates the display device 170 as including a first display 171 and a second display 172. The first display 171 and the second display 172 may display different kinds of X-ray images. For example, the first display 171 may display 2D projection images and the second display 172 may display 3D images or 3D stereoscopic images. Otherwise, the first display 171 and the second display 172 may display one kind of X-ray image.

The external appearance of the X-ray imaging apparatus 100 in accordance with an exemplary embodiment has been described. Hereinafter, rotation methods of the gantry 102 will be described with reference to FIGS. 2A and 2B.

The gantry 102 may be rotated about the bore 105 twice in a first direction during 2 cardiac cycles. That is, the gantry 102 may be rotated once per cardiac cycle. Hereinafter, the cardiac cycle will be described in brief.

The human heart consists of two atria and two ventricles. The heart beats in a designated cycle, and a period from one heartbeat to the next heartbeat is referred to as a cardiac cycle. A single cardiac cycle may be divided into an atrial systolic phase, a ventricular systolic phase, and an atrial and ventricular diastolic phase. In the atrial systolic phase, the left atrium and the right atrium contract and the left ventricle and the right ventricle relax. In the ventricular systolic phase, the left atrium and the right atrium relax and the left ventricle and the right ventricle contract. In the atrial and ventricular diastolic phase, all of the left atrium, the right atrium, the left ventricle, and the right ventricle relax.

An electrocardiogram (ECG) is a diagram in which action current and action potential according to contraction of the heart are recorded as waveform curves. In an ECG waveform, upward regions and downward regions alternately appear, and these regions are sequentially referred to as P, Q, R, S, and T waves.

In the ECG waveform, the P wave is generated during atrial depolarization. A QRS-complex is generated during ventricular depolarization. Further, the T wave is generated during ventricular repolarization.

The P wave may be understood as a waveform recording a contraction process of the left and right atria. The QRS-complex may be understood as a waveform recording a contraction process of the left and right ventricles. The T wave may be understood as a waveform recording a relaxation process of the left and right ventricles.

A period during which one wave is repeated is referred to as a cardiac cycle.

In accordance with an exemplary embodiment, the position of the X-ray generator 110 when first rotation of the gantry 102 is started and the position of the X-ray generator 110 when second rotation of the gantry 102 is started are different. Hereinafter, the position of the X-ray generator 110 when first rotation of the gantry 102 is started will be defined as a 'first position'. Further, the position of the X-ray generator 110 when second rotation of the gantry 102 is started will be defined as a 'second position'.

Figure 2A:
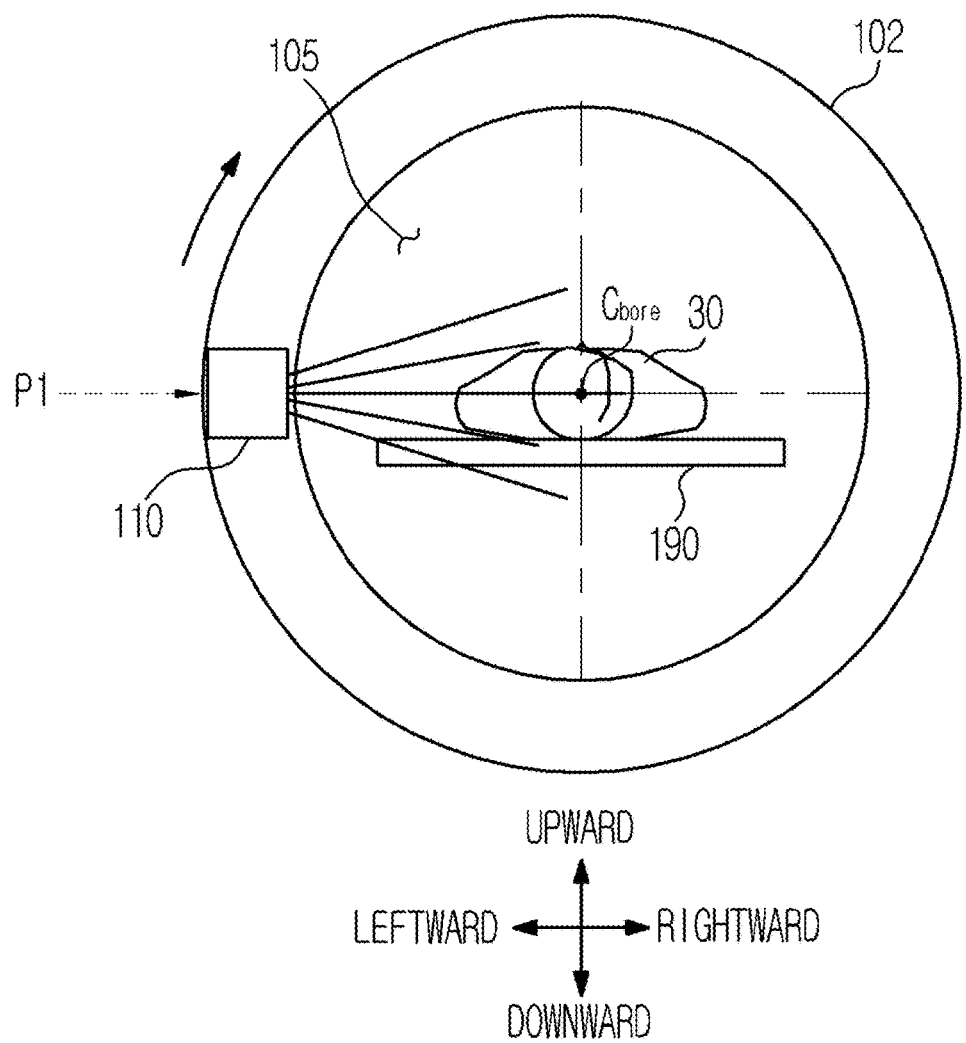
FIGS. 2A and 2B are views illustrating gantry rotation methods in the X-ray imaging apparatus.

FIG. 2A exemplarily illustrates the first position of the X-ray generator 110. FIG. 2A illustrates the first position as being set to a left horizontal point P1 of the object 30. When a cardiac cycle is started under the condition that the X-ray generator 110 is located at the first position, the gantry 102 is rotated in the first direction about the bore 105. While the gantry 102 is rotated, the X-ray generator 110 applies X-rays to the object 30 plural times, and the X-ray detector 120 detects X-rays transmitted through the object 30. As a result, a plurality of 2D projection images is acquired. For example, about 1,000 2D projection images may be acquired.

Figure 2B:
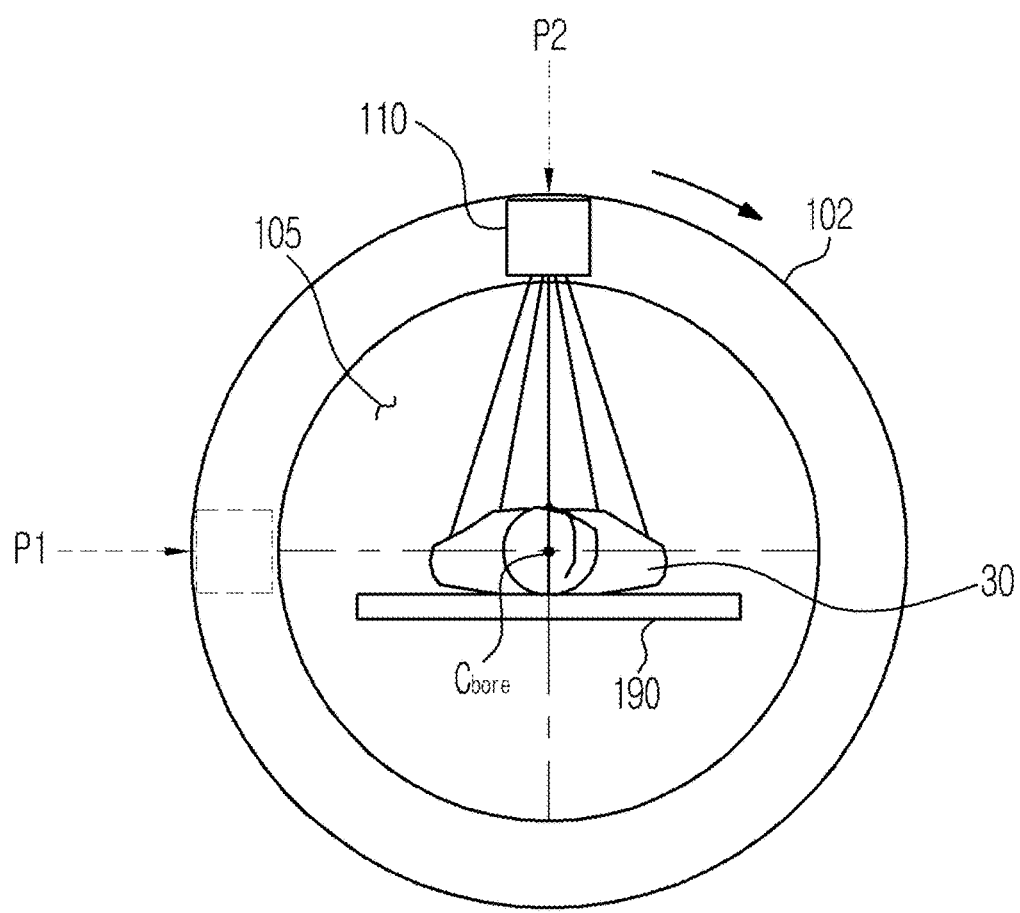

FIG. 2B exemplarily illustrates the second position of the X-ray generator 110. FIG. 2B illustrates the second position as being a position P2 rotated in the first direction about the bore 105 from the first position P1 by an angle of 90 degrees. When a new cardiac cycle is started under the condition that the X-ray generator 110 is located at the second position, the gantry 102 is rotated in the first direction about the bore 105. While the gantry 102 is rotated, the X-ray generator 110 applies X-rays to the object 30 plural times, and the X-ray detector b 120 detects X-rays transmitted through the object 30. As a result, a plurality of 2D projection images is acquired. For example, about 1,000 2D projection images may be acquired.

When rotation of the gantry 102 is started from different positions according to cardiac cycles, acquisition of 2D projection images including redundant information in the same cardiac phase of the respective cardiac cycles may be reduced.

FIGS. 2A and 2B illustrate that the central angle between the first and second positions is 90 degrees. However, the central angle between the first and second positions is not limited to 90 degrees. For example, it may be understood that the central angle between the first and second positions which is within 180 degrees is within the scope of the disclosure. The central angle between the first and second positions may be set in advance by an operator.

As the gantry 102 is rotated twice during 2 cardiac cycles, as described above, X-rays are applied to the object 30 and as a result, a plurality of 2D projection images is acquired in each cardiac cycle. As one example, the plurality of 2D projection images may be acquired during 2 continuous cardiac cycles in the ECG. As another example, the plurality of 2D projection images may be acquired during 2 non-continuous cardiac cycles in the ECG. Whether or not a plurality of 2D projection images is acquired during 2 continuous cardiac cycles or a plurality of 2D projection images is acquired during 2 non-continuous cardiac cycles in the ECG may be set in advance by an operator.

According to methods of acquiring 2D projection images, rotation methods of the gantry 102 may be different.

As one example, if a plurality of 2D projection images is acquired during 2 continuous cardiac cycles in the ECG, first rotation and second rotation of the gantry 102 may be continuously performed at a regular speed. Further, in the first rotation and the second rotation, the gantry 102 may be rotated by an angle of greater than 360 degrees.

In more detail, the first rotation of the gantry 102 is performed during a first cardiac cycle. During the first cardiac cycle, the gantry 102 is rotated from when the X-ray generator 110 starts to rotate from the first position in the first direction to when the X-ray generator 110 reaches the second position. That is, in the first rotation, the gantry 102 is rotated by an angle of 450 degrees about the bore 105. If the gantry 102 is rotated in such a manner, the X-ray generator 110 is located at the second position when the first rotation of the gantry 102 has been completed. Therefore, as a second cardiac cycle continuous with the first cardiac cycle is started, the second rotation of the gantry 102 may be immediately started. During the second cardiac cycle, the gantry 102 may be rotated from the second position by an angle of 450 degrees in the first direction.

As another example, if a plurality of 2D projection images is acquired during 2 non-continuous cardiac cycles in the ECG, rotation of the gantry 102 may be performed in 3 stages.

In more detail, first rotation of the gantry 102 is performed during a first cardiac cycle in the ECG. During the first cardiac cycle, the gantry 102 is rotated from when the X-ray generator 110 starts to rotate from the first position in the first direction to when the X-ray generator 110 again reaches the first position. That is, in the first rotation, the gantry 102 is rotated by an angle of 360 degrees about the bore 105. Thereafter, during a second cardiac cycle continuous with the first cardiac cycle, the gantry 102 is rotated so that the X-ray generator 110 is rotated from the first position and then reaches the second position. Thereafter, a third cardiac cycle continuous with the second cardiac cycle is started, and a second rotation of the gantry 102 is started. During the third cardiac cycle, the gantry 102 is rotated from when the X-ray generator 110 starts to rotate from the second position in the first direction to when the X-ray generator again reaches the second position. That is, in the second rotation, the gantry 102 is rotated by an angle of 360 degrees about the bore 105.

Among the gantry rotation methods in accordance with the exemplary embodiments, in case of the former, the gantry 102 is rotated by an angle of 450 degrees when the gantry 102 is rotated once, and thus, the rotation speed of the gantry 102 in the former may be set to be higher than that of the gantry 102 in the latter. Further, in case of the former, the gantry 102 is rotated continuously two times at a regular speed, and thus, rotation of the gantry 102 in the former may be more natural than rotation of the gantry 102 in the latter. Hereinafter, the former, i.e., the case in that the gantry 102 is continuously rotated two times at a regular speed, will be exemplarily described.

Figure 3:
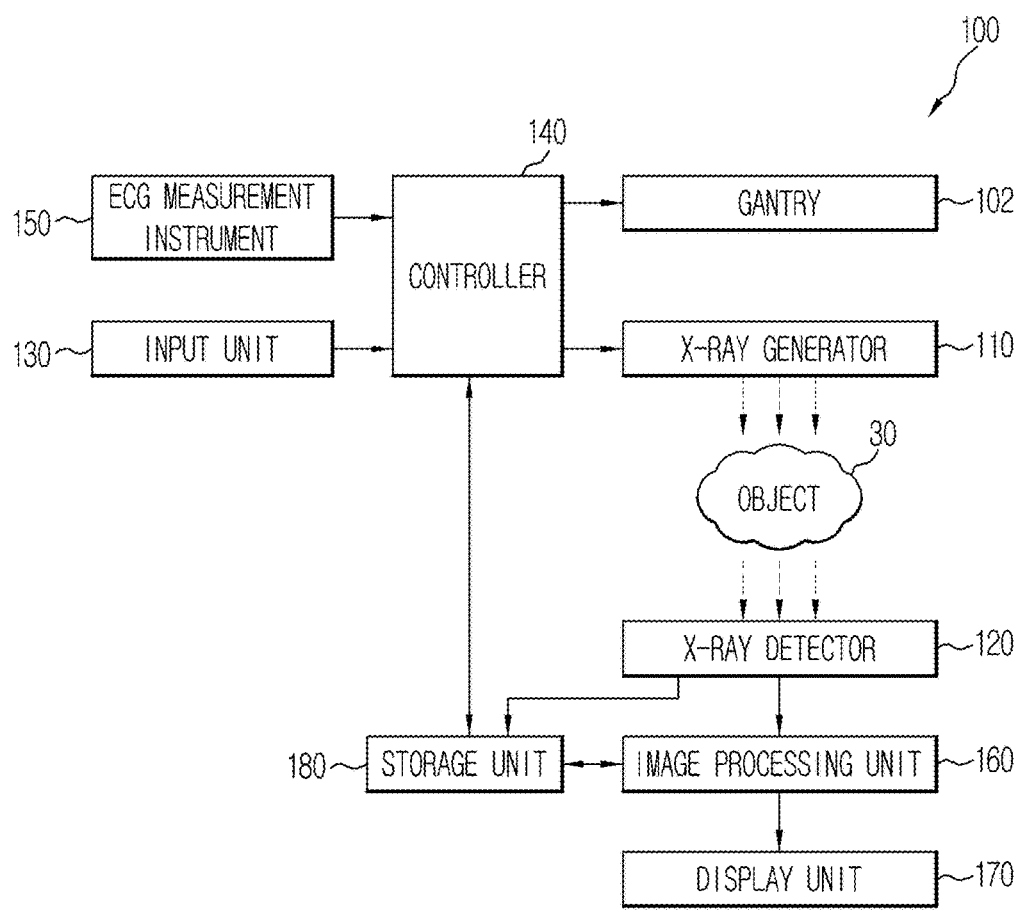
FIG. 3 is a block diagram of the control configuration of the X-ray imaging apparatus in accordance with an exemplary embodiment.

FIG. 3 is a block diagram of the control configuration of the X-ray imaging apparatus 100 in accordance with an exemplary embodiment.

As exemplarily shown in FIG. 3, the X-ray imaging apparatus 100 may include the input unit 130, an ECG measurement instrument 150, a controller 140, the gantry 102, the X-ray generator 110, the X-ray detector 120, the image processing unit 160, the display unit 170, and a storage unit 180.

The input unit 130 may receive instructions or a command to control operations of the X-ray imaging apparatus 100 and data to be used to control operations of the X-ray imaging apparatus 100 from an operator, as described above. For example, the input unit 130 may receive a command to adjust the position of the table 190, information regarding the central angle between the first position and the second position, and information regarding the method of acquiring a plurality of 2D projection images.

The ECG measurement instrument 150 may measure the ECG of the object 30. For example, the ECG measurement instrument 150 may include at least one electrode attached to a region around the heart of the object 30, a main body, and a lead connecting the at least one electrode and the main body. A signal measured by the ECG measurement instrument 150 is provided to the controller 140, which will be described later.

The X-ray generator 110 generates X-rays and applies the X-rays to the object 30. The X-ray generator 110 may include an X-ray tube generating X-rays. Hereinafter, a more detailed description of the X-ray tube will be given with reference to FIG. 4.

Figure 4:
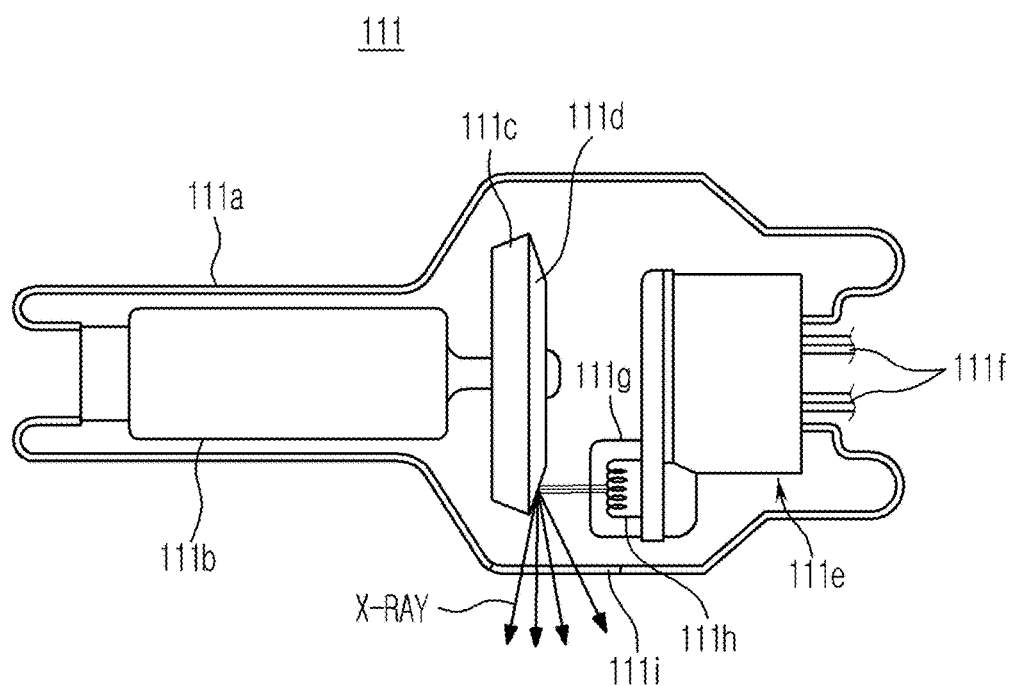
FIG. 4 is a view schematically illustrating the structure of an X-ray tube included in an X-ray generator.

FIG. 4 is a view schematically illustrating the structure of the X-ray tube included in the X-ray generator 110.

With reference to FIG. 4, the X-ray tube 111 may be implemented as a diode vacuum including an anode 111c and a cathode 111e. As a tubular body, a glass tube 111a formed of hard silicate glass may be used.

The cathode 111e includes a filament 111h and a focusing electrode 111g to focus electrons. The focusing electrode 111g may be referred to as a focusing cup. A high vacuum state of about 10 mmHg is formed within the glass tube 111a and the filament 111h of the cathode 111e is heated to a high temperature, thus generating thermal electrons. For example, a tungsten filament may be used as the filament 111h and current may be applied to electric wires 111f connected to the filament 111h so as to heat the filament 111h. However, exemplary embodiments are not limited to employment of the filament 111h in the cathode 111e, and a carbon nano-tube which may be driven by a high speed pulse may be used as the cathode 111e.

The anode 111c is mainly formed of copper, and a target material 111d is applied to or disposed at a portion of the anode 111c facing the cathode 111e. For example, a high resistance material, for example, Cr, Fe, Co, Ni, W, or Mo, may be used as the target material 111d. As the melting point of the target material 111d is higher, a focal spot size is reduced.

When high voltage is applied between the cathode 111e and the anode 111c, thermal electrons are accelerated and collide with the target material 111d of the anode 111c, thus generating X-rays. The generated X-rays are radiated to the outside through a window 111i. The window 111i may be formed of a beryllium (Be) thin film. A filter (not shown) may be located on the front or rear surface of the window 111i to filter out X-rays of a specific energy band.

The target material 111d may be rotated by a rotor 111b. When the target material 111d is rotated, a thermal accumulation rate may increase 10 times or more and the focal spot size may be reduced, as compared to a case in which the target material 111d is fixed.

Voltage applied between the cathode 111e and the anode 111c of the X-ray tube 111 is referred to as tube voltage. The intensity of the tube voltage may be expressed as a peak value (unit: kVp).

As tube voltage increases, the velocity of thermal electrons increases. As a result, the energy of X-rays generated by collision of the thermal electrons with the target material 111d (the energy of photons) increases. When the energy of X-rays increases, the amount of X-rays transmitted through the object 30 increases. When the transmission amount of X-rays increases, the amount of X-rays detected by the X-ray detector 120 increases. Consequently, an X-ray image having a high signal to noise ratio (SNR), i.e., a high quality X-ray image, may be acquired.

On the other hand, as tube voltage decreases, the velocity of thermal electrons decreases and the energy of X-rays generated by collision of the thermal electrons with the target material 111d decreases. As the energy of X-rays decreases, the amount of X-rays absorbed by the object 30 increases and the amount of X-rays detected by the X-ray detector 120 decreases. Consequently, an X-ray image having a low SNR, i.e., a low quality X-ray image, is acquired.

Current flowing in the X-ray tube 111 is referred to as tube current, and the intensity of tube current may be expressed as a mean value (unit: mA). As tube current increases, the amount of X-rays (the number of photons: an X-ray dose) increases and an X-ray image having a high SNR is acquired. On the other hand, as tube current decreases, the amount of X-rays decreases and an X-ray image having a low SNR is acquired.

In summary, the energy of X-rays may be controlled by adjusting tube voltage. Further, the dose or intensity of X-rays may be controlled by adjusting tube current and X-ray exposure time. Therefore, the energy or dose of radiated X-rays may be controlled by controlling tube voltage or tube current according to kind and characteristics of the object 30.

X-rays radiated by the X-ray generator 110 have a constant energy band. The energy band may be defined by an upper limit and a lower limit. The upper limit of the energy band, i.e., the maximum energy of radiated X-rays, may be adjusted by the intensity of tube voltage. The lower limit of the energy band, i.e., the minimum energy of radiated X-rays, may be adjusted by a filter (not shown) provided on the X-ray generator 110. When the filter filters out X-rays of a lower energy band, the mean energy of the radiated X-rays may be increased. Further, the energy of the radiated X-rays may be represented by the maximum energy or the mean energy.

Referring to FIG. 3 again, the X-ray detector 120 detects X-rays transmitted through the object 30 and converts the X-rays into electrical signals. Hereinafter, a more detailed description of the X-ray detector 120 will be given with reference to FIG. 5.

Figure 5:
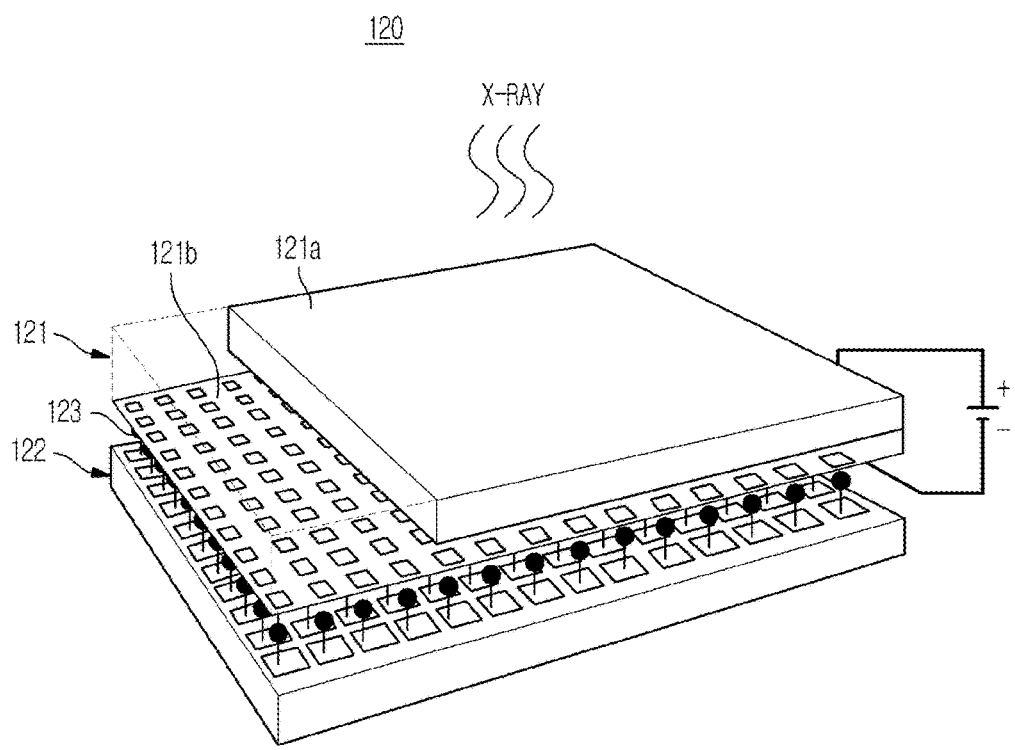
FIG. 5 is a view illustrating the structure of an X-ray detector.

With reference to FIG. 5, the X-ray detector 120 includes a light receiving element 121 to detect X-rays and convert the detected X-rays to electrical signals, and a readout circuit 122 to read the electrical signals. Here, the readout circuit 122 is formed in a 2D pixel array structure including a plurality of pixel areas. The light receiving element 121 may be formed of a single crystal semiconductor material so as to assure high resolution, rapid response time, and a high dynamic area at a low energy and a low dose. For example, the single crystal semiconductor material may be Ge, CdTe, CdZnTe, or GaAs.

The light receiving element 121 may be formed in a PIN photo diode type by bonding a p-type layer 121b, in which a p-type semiconductor is arranged in a 2D pixel array structure, to the lower surface of a high-resistance n-type semiconductor substrate 121a. The readout circuit 122 formed using a CMOS process is combined with the light receiving element 121 at respective pixels. The CMOS readout circuit 122 and the light receiving element 121 may be bonded through a flip chip bonding method. In more detail, the CMOS readout circuit 122 and the light receiving element 121 may be bonded using bumps 123 formed of solder (PbSn) or indium (In) through reflow and thermo-compression. The above-described structure is only one example of the X-ray detector 120 and the structure of the X-ray detector 120 is not limited thereto.

Referring to FIG. 3 again, the controller 140 may acquire information regarding a cardiac cycle by analyzing the ECG signal received from the ECG measurement instrument 150. When the information regarding the cardiac cycle is acquired, the controller 140 may determine the rotation speed of the gantry 102 according to the cardiac cycle. For example, if the cardiac cycle is 1 second, the controller 140 may determine the rotation speed of the gantry 102 so that the gantry 102 is rotated by 450 degrees for 1 second. When the rotation speed of the gantry 102 is determined, the controller 140 may rotate the gantry 102 according to the cardiac cycle.

Further, the controller 140 may control tube current of the X-ray generator 110 so that X-rays of different doses are applied according to cardiac phases.

In more detail, the controller 140 controls tube current of the X-ray generator 110 so that X-rays of a reference dose are radiated in a cardiac phase, in which movement of the heart is the least, during the cardiac cycle. For example, the cardiac phase, in which movement of the heart is the least, during the cardiac cycle may be a cardiac phase when the heart is maximally contracted or a cardiac phase when the heart is maximally relaxed. Hereinafter, the cardiac phase when the heart is maximally contracted will be defined as 'the first cardiac phase'. Further, the cardiac phase when the heart is maximally relaxed will be defined as 'the second cardiac phase'. With reference to the cardiac signal, the QRS-complex corresponds to the first cardiac phase, and a section after the T wave corresponds to the second cardiac phase.

The controller 140 controls tube current of the X-ray generator 110 so that X-rays of a dose less than the reference dose are radiated in cardiac phases except for the first cardiac phase and the second cardiac phase during the cardiac cycle. It may be understood that the reference dose is a dose of a level which is used in general cardiac CT.

Figure 6:
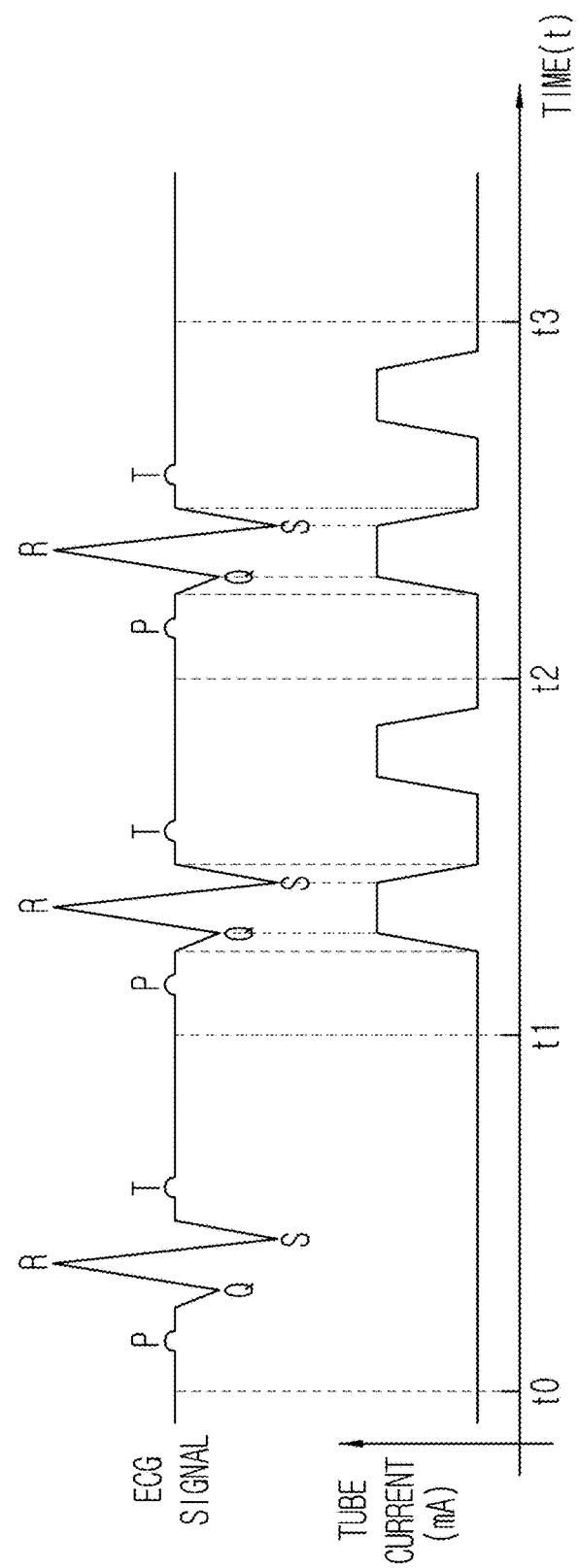
FIG. 6 is a view illustrating an X-ray dose adjustment method.

With reference to FIG. 6, it may be confirmed that tube current maintains a reference value in the QRS-complex and the section after the T wave during the cardiac cycle. Further, it may be confirmed that tube current maintains a value lower than the reference value in the remaining sections except for the QRS-complex and the section after the T wave during the cardiac cycle so that X-rays of a dose less than the reference dose may be radiated in the remaining sections.

As described above, if tube current is controlled according to cardiac phases within the cardiac cycle, a radiation dose applied to a patient or medical staff may be reduced, as compared to the case in that tube current maintains the reference value throughout the cardiac cycle.

Referring to FIG. 3 again, the image processing unit 160 may generate a plurality of 2D projection images based on electrical signals output from the respective pixels of the X-ray detector 120. Further, the image processing unit 160 may generate a 4D image of the heart by performing image reconstruction of the plurality of 2D projection images. The image processing unit 160 may use, for example, a prior image-based compressed sensing image reconstruction algorithm.

The prior image-based compressed sensing image reconstruction algorithm may precisely reconstruct a dynamic 4D image from a small number of 2D projection images. In the prior image-based compressed sensing image reconstruction algorithm, prior images are reconstructed from undersampled data sets, and a target image is acquired using the prior images. Hereinafter, the prior image-based compressed sensing image reconstruction algorithm will be described in more detail.

First, compressed sensing will be described. Based on the standard image reconstruction theory in medical images, in order to avoid aliasing artifacts, a sampling rate should satisfy the Shannon-Nyquist sampling theorem. The Shannon-Nyquist sampling theorem states that, when a signal is sampled, a sampling frequency should be at least two times the maximum frequency included in such a signal. When sampling is performed in such a manner, the original signal may be reconstructed from the sampled signal.

However, the Shannon-Nyquist sampling theorem does not assume any prior information of an image. Therefore, if prior information is used during an image reconstruction process, an image may be precisely reconstructed although the Shannon-Nyquist sampling rate is not satisfied.

Compressed sensing is performed so as to systematically and precisely reconstruct a sparse image from the undersampled data sets. Here, the undersampled data set means a data set sampled at a sampling rate less than the Shannon-Nyquist sampling rate.

Sparsity means that the number of meaningful constituent elements (for example, constituent elements other than 0) is relatively small, as compared to a signal length. For example, if constituent elements of a signal x are as follows, such a signal may be regarded as a sparse signal.

$$x=[1,0,10,0,0,0,0,0,\ldots,0,0]$$

Sparsity of a signal is expressed as $I_p$-norm. For example, $I_0$-norm means the number of constituent elements other than 0 among the constituent elements of x. On the other hand, $I_1$-norm means the sum of the absolute values of the constituent elements other than 0 among the constituent elements of x. If $x=[1, -1, 2, 0]$, $I_0$-norm=3 and $I_1$-norm=4.

A real medical image may not be a sparse signal. For example, in case of a CT image, an image prior to injection of a contrast medium or an image after injection of the contrast medium may be a sparse signal. When mathematical transforms are applied to a medical image which is not a sparse signal, the corresponding signal may be converted into a sparse signal. Such mathematical transforms to convert an image which is not a sparse signal into a sparse signal are referred to as sparsifying transforms. As examples of the sparsifying transforms, there are a discrete gradient transform and a wavelet transform.

The discrete gradient transform may be expressed by Equation 1 below.

$$\nabla_{m,n} X(m,n) = \sqrt{(D_x X)^2 + (D_y X)^2} \quad \text{[Equation 1]}$$

In Equation 1, X(m,n) represents an image value at a pixel (m,n). $D_x X = X(m+1,n) - X(m,n)$ and $D_y X = X(m,n+1) - X(m,n)$. If a result acquired by applying the discrete gradient transform expressed by Equation 1 to an original image is referred to as a discrete gradient image, the discrete gradient image becomes sparse three times, as compared to the original image.

In compressed sensing image reconstruction, instead of directly reconstructing a target image, the sparsified image of the target image is reconstructed. After the sparsified image is reconstructed, an inverse sparsifying transform is used to transform the sparsified image back to the target image.

The sparsifying transform is denoted as $\Psi$. Compressed sensing image reconstruction is implemented by solving a minimization problem of Equation 2 below.

$$\min_X |\Psi X|_{l_1}, \quad \text{[Equation 2]}$$
$$\text{subject to } AX = Y$$

In Equation 2, $|z_{l_1}| = \sum_{i=1}^{N} |z_i|$ is $l_1$ norm of an N-dimensional vector z. A vector X is a vectorized target image. A matrix A is a system matrix describing an X-ray projection measurement instrument. A vector Y represents a line integral value. In compressed sensing image reconstruction, among all images satisfying AX=Y, an image minimizing $l_1$ norm of the sparsified image is selected.

In the prior image-based compressed sensing image reconstruction algorithm, the prior image $X_p$ may be reconstructed from projection images, for example, using a standard filtered back projection (FBP) reconstruction algorithm. The prior image $X_p$ may be used to limit a compressed sensing image reconstruction method. In the reconstructed prior image, dynamic information is lost but static structures in the image may be reconstructed without artifacts due to undersampling.

In a subtraction image $X-X_p$, acquired by subtracting the prior image $X_p$ from the target image X, all static structures of the target image X are removed and only dynamic constituent elements of the target image X remain. Due to such a subtraction operation, the target image X may be sparsified. Thereafter, the sparsifying transform $\Psi$ may be applied to the subtraction image $X-X_p$. In summary, the prior image-based compressed sensing image reconstruction algorithm may be implemented by solving a restricted minimization problem of Equation 3 below.

$$\min_X \left[ \alpha |\Psi_1 (X - X_P)|_{l_1} + (1 - \alpha) |\Psi_2 X|_{l_1} \right], \quad \text{[Equation 3]}$$

subject to $AX = Y$

In Equation 3, a vector X means a vectorized target image. A vector $X_p$ represents a vectorized prior image. $\Psi_1$ and $\Psi_2$ represent sparsifying transforms. For example, the discrete gradient transform may be used as $\Psi_1$ and $\Psi_2$. A control parameter $\alpha$ may be set to a number less than 1. If $\alpha$ is set to 0, Equation 3 and Equation 2 become equal.

Figure 7:
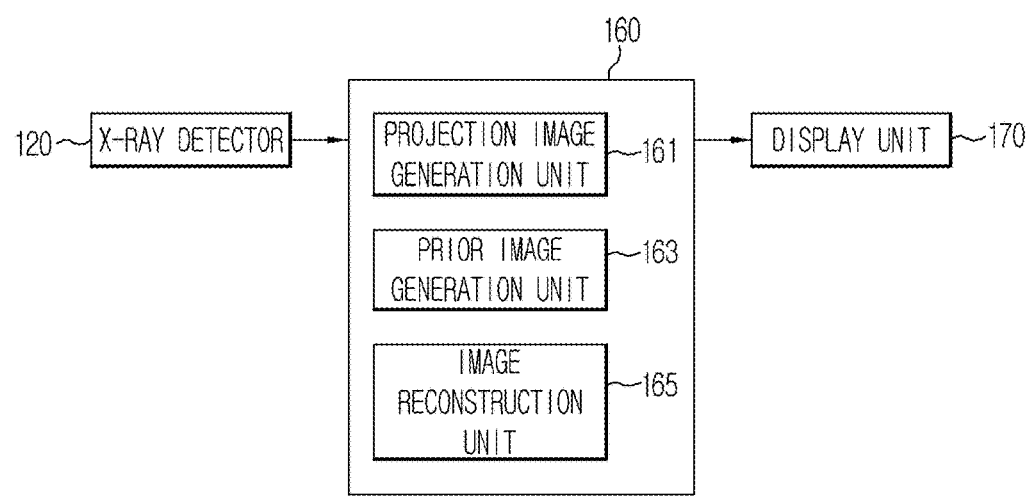
FIG. 7 is a view illustrating the detailed configuration of an image processing unit shown in FIG. 3.

FIG. 7 is a view illustrating the detailed configuration of the image processing unit 160.

As exemplarily shown in FIG. 7, the image processing unit 160 may include a projection image generation unit 161, a prior image generation unit 163 (e.g., prior image generator), and an image reconstruction unit 165 (e.g., image reconstructor).

The projection image generation unit 161 may generate 2D projection images based on electrical signals output from the respective pixels of the X-ray detector 120. As described above, while the gantry 102 is rotated about the bore 105, the X-ray generator 110 applies X-rays to the object 30 plural times. As a result, a plurality of 2D projection images of the object 30 is acquired. For example, while the gantry 105 is rotated one time, 1,000 2D projection images may be acquired.

The prior image generation unit 163 may select 2D projection images according to a designated reference from among 2D projection images acquired during 2 cardiac cycles, and generate prior images by performing image reconstruction of the selected 2D projection images. The prior images are images which may be used as prior information when 3D volumes according to respective cardiac phases are reconstructed. That is, the prior images are images to be used when 3D images according to the cardiac phases are generated.

The prior image generation unit 163 may generate a first prior image corresponding to the first cardiac phase and a second prior image corresponding to the second cardiac phase. The first prior image and the second prior image may be generated using the same method. Hereinafter, a method of generating the first prior image will be described.

First, the prior image generation unit 163 selects 2D projection images acquired within a regular scan range based on a point corresponding to the first cardiac phase among the overall scan range of the X-ray generator 110.

Figure 8:
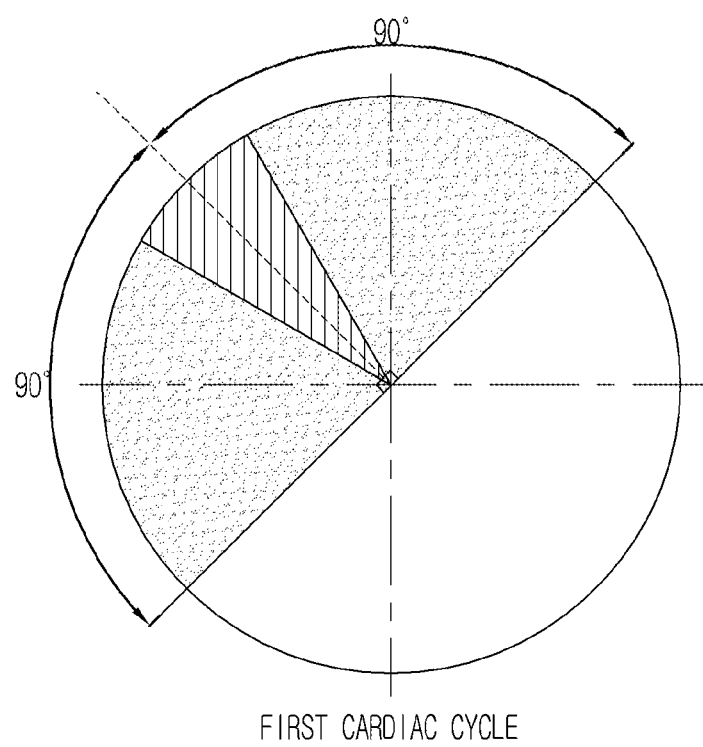
FIG. 8 is a view illustrating a projection image selection method in accordance with an exemplary embodiment, to be used to generate a first prior image.

As one example, 2D projection image selection may be carried out with respect to 2D projection images acquired during a first cardiac cycle. FIG. 8 exemplarily illustrates a case in which 2D projection image selection to be used to generate the first prior image is carried out with respect to 2D projection images acquired during the first cardiac cycle. With reference to FIG. 8, it may be confirmed that 2D projection images acquired within a scan range of 180 degrees based on the point corresponding to the first cardiac phase among the overall scan range of the X-ray generator 110 are selected.

As another example, 2D projection image selection may be carried out with respect to 2D projection images acquired during a second cardiac cycle.

Figure 9:
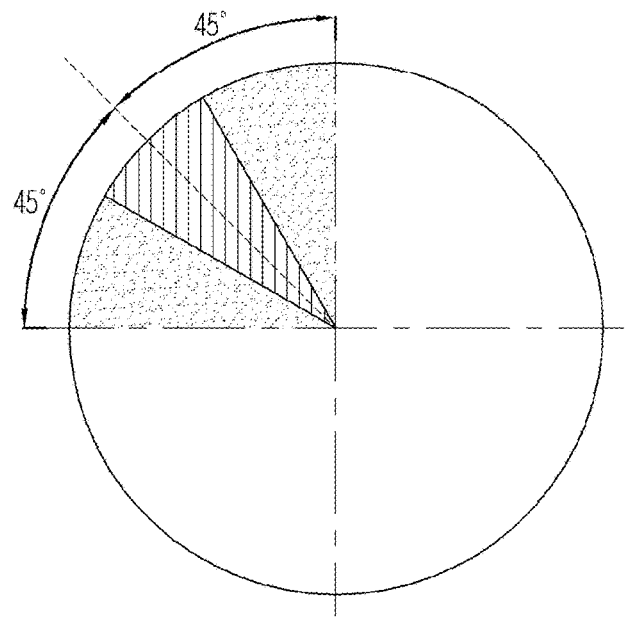
FIG. 9 is a view illustrating a projection image selection method in accordance with another exemplary embodiment, to be used to generate a first prior image.
Figure 9:
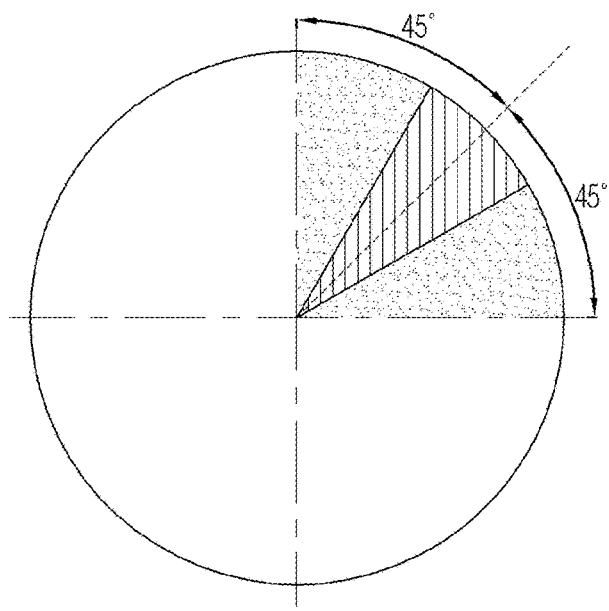

As yet another example, 2D projection image selection may be carried out with respect to 2D projection images acquired during the first cardiac cycle and 2D projection images acquired during the second cardiac cycle. FIG. 9 exemplarily illustrates a case in which 2D projection image selection to be used to generate the first prior image is carried out with respect to 2D projection images acquired during the first cardiac cycle and 2D projection images acquired during the second cardiac cycle.

With reference to FIG. 9, it may be confirmed that 2D projection images acquired within a scan range of 90 degrees based on the point corresponding to the first cardiac phase from among 2D projection images acquired during the first cardiac cycle are selected. Further, it may be confirmed that 2D projection images acquired within a scan range of 90 degrees based on the point corresponding to the first cardiac phase from among 2D projection images acquired during the second cardiac cycle are selected.

When 2D projection image selection has been completed, the prior image generation unit 163 reconstructs a 3D volume of the first cardiac phase from the selected 2D projection images. A result of reconstruction may be understood as the first prior image.

The prior image generation unit 163 may reconstruct the second prior image using the same method as the first prior image generation method. One of the first prior image and the second prior image may be first generated and the other may be then generated in such a manner, or the first prior image and the second prior image may be simultaneously generated.

When the first prior image and the second prior image are generated, if the 2D projection images selected in the method shown in FIG. 9 are used, temporal resolution may be improved, as compared to the case in which the 2D projection images selected in the method shown in FIG. 8 are used.

Referring to FIG. 7 again, the image reconstruction unit 165 groups the 2D projection images, acquired during 2 cardiac cycles, into 2D projection images acquired in the same cardiac phases. Thereafter, the image reconstruction unit 165 performs image reconstruction according to cardiac phases. When image reconstruction has been completed, 3D images similar to the actual heart may be acquired according to cardiac phases.

The image reconstruction unit 165 may use the prior image-based compressed sensing image reconstruction algorithm when image reconstruction according to cardiac phases is performed. As described above, the prior image-based compressed sensing image reconstruction algorithm uses information regarding the prior image of a target image during image reconstruction. When the prior image-based compressed sensing image reconstruction algorithm is used, although image reconstruction is performed using only a small number of 2D projection images, a high-quality 3D image may be acquired.

During image reconstruction, which one is used from among the first prior image and the second prior image may be determined according to a section of the cardiac cycle in which the cardiac phase in which image reconstruction will be performed is acquired. A detailed description thereof will be given with reference to FIG. 10.

Figure 10:
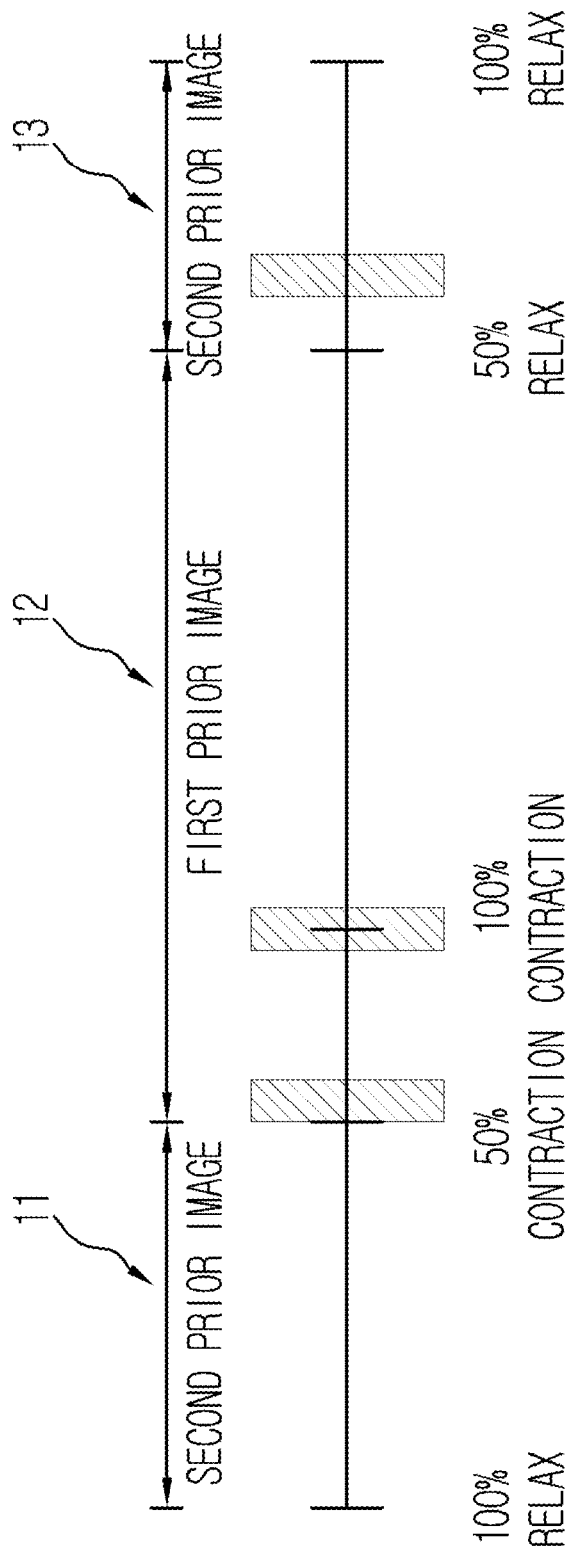
FIG. 10 is a view illustrating which kind of prior image is applied to image reconstruction in a cardiac phase corresponding to each section, when a cardiac cycle is divided into a plurality of sections.

FIG. 10 illustrates the cardiac cycle divided into a first section 11, a second section 12, and a third section 13. The first section 11 refers to a section from when the heart is relaxed by 100% to when the heart is contracted by 50%. The second section 12 refers to a section from when the heart is contracted by 50% to when the heart is relaxed by 50%. The third section 13 refers to a section from when the heart is relaxed by 50% to when the heart is relaxed by 100%.

In this case, when image reconstruction is performed in the cardiac phase corresponding to the first section 11 and the cardiac phase corresponding to the third section 13, the second prior image may be used. On the other hand, when image reconstruction is performed in the cardiac phase corresponding to the second section 12, the first prior image may be used.

As described above, when 3D images according to cardiac phases are acquired using the first prior image and the second prior image, the image reconstruction unit 165 may generate a dynamic 4D image by arranging the 3D images, acquired according to the cardiac phases, in temporal order.

Figure 11:
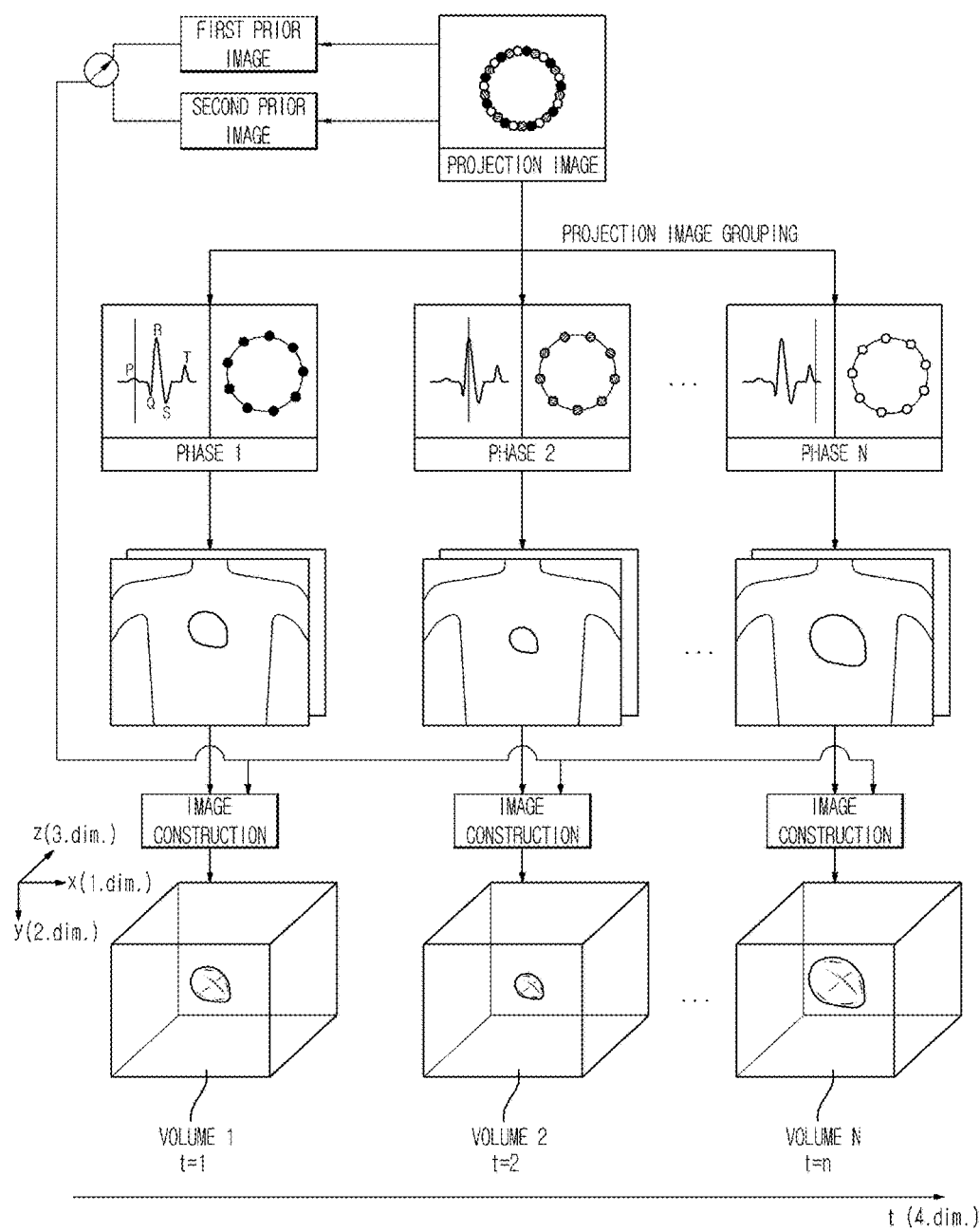
FIG. 11 is a view illustrating the overall operation process of the image processing unit.

FIG. 11 is a view illustrating the overall operation process of the image processing unit 160.

FIG. 11 illustrates grouping 2D projection images acquired during 2 cardiac cycles into 2D projection images acquired in the same cardiac phases, performance of image reconstruction according to cardiac phases using one of the first prior image and the second prior image, and arrangement of 3D images, acquired according to the cardiac phases, in temporal order.

From FIG. 11, it may be confirmed that the cardiac cycle is divided into n cardiac phases (a phase 1, a phase 2, ..., a phase n). Further, it may be confirmed that n 3D images (a volume 1, a volume 2, ..., a volume n) corresponding to the n cardiac phases (the phase 1, the phase 2, ..., the phase n) are acquired. Then, it may be confirmed that the n 3D images (the volume 1, the volume 2, ..., the volume n) are arranged according to time.

Referring to FIG. 3 again, the storage unit 180 may store various pieces of data and algorithms. For example, the storage unit 180 may store various pieces of set information regarding the operation of the X-ray imaging apparatus 100, input by an operator.

The storage unit 180 may store at least one of an algorithm to analyze the ECG signal, an algorithm to calculate the rotation speed of the gantry 102, an algorithm to be used to generate the first prior image or the second prior image, and an algorithm required to perform image reconstruction according to cardiac phases.

The storage unit 180 may store images generated by the image processing unit 160, for example, 2D projection images, the first prior image, the second prior image, 3D images according to cardiac phases, and a 4D image of the heart.

The storage unit 180 may be a volatile memory device, a nonvolatile memory device, a hard disk, an optical disc, or a combination thereof. However, the storage unit 180 is not limited thereto and may be implemented as many different types of memories known in the art.

The display unit 170 may display the images generated by the image processing unit 160. For example, the display unit 170 may display at least one of 2D projection images acquired during 2 cardiac cycles, 3D images reconstructed according to cardiac phases, and a 4D image of the heart.

The control configuration of the X-ray imaging apparatus 100 has been described above. Hereinafter, with reference to FIG. 10 and FIGS. 12 to 14B, result images acquired by the X-ray imaging apparatus 100 will be described.

Figure 12:
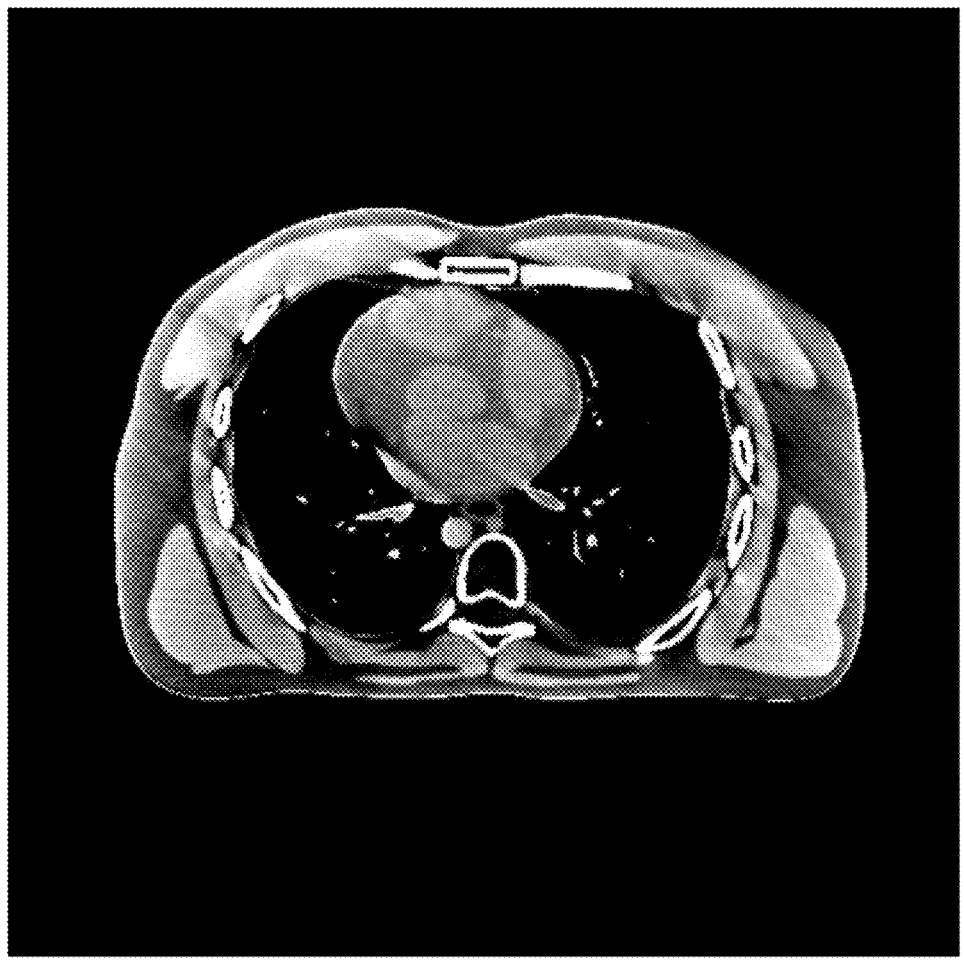
FIG. 12 is a view exemplarily illustrating a first prior image.

FIG. 12 is a view exemplarily illustrating the first prior image.

Figure 13A:
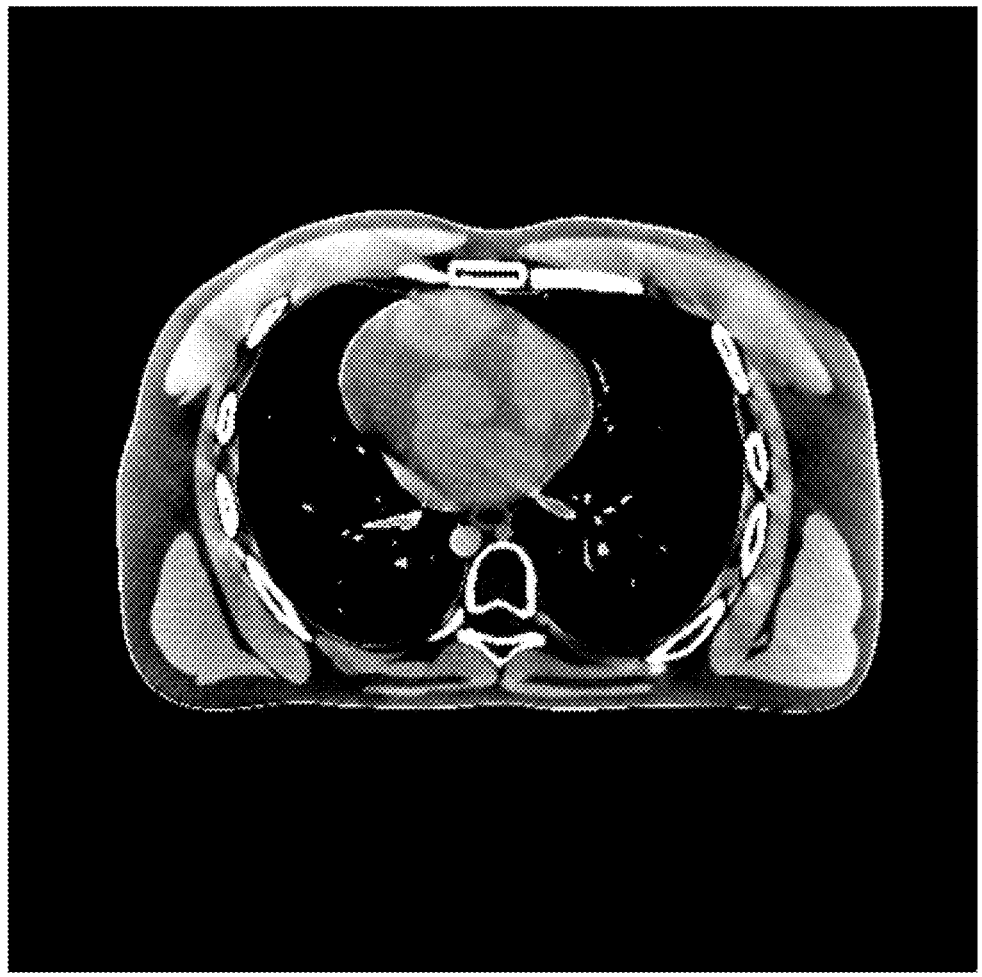
FIG. 13A is a view exemplarily illustrating a result of image reconstruction performed based on 2D projection images acquired during 1 cardiac cycle.
Figure 13B:
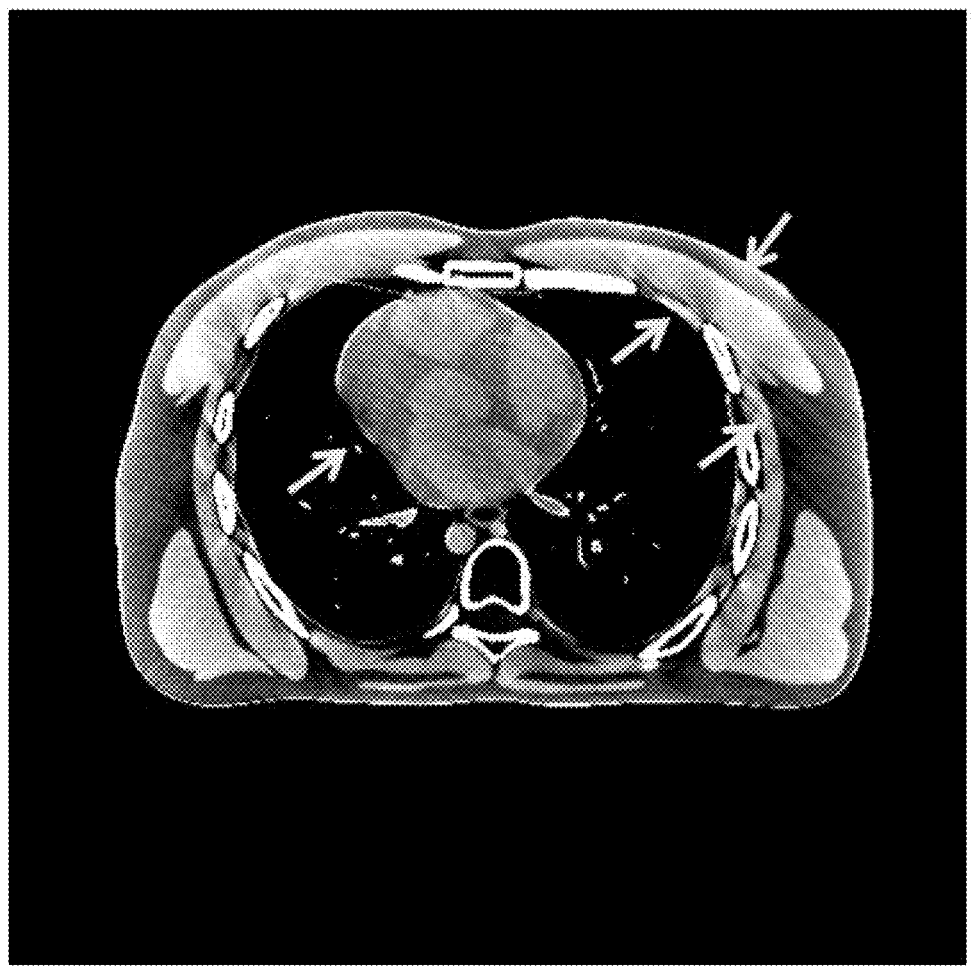
FIG. 13B is a view exemplarily illustrating a result of image reconstruction performed based on 2D projection images acquired during 2 cardiac cycles.

FIGS. 13A and 13B are views exemplarily illustrating results of image reconstruction of the cardiac phase when the heart is contracted by 100%. With reference to FIG. 10, the cardiac phase when the heart is contracted by 100% corresponds to the second section 12 of the cardiac cycle. Therefore, when image reconstruction in the corresponding cardiac phase is performed, the first prior image of FIG. 12 is used.

FIG. 13A exemplarily illustrates a result of image reconstruction performed based on 2D projection images acquired during 1 cardiac cycle. FIG. 13B exemplarily illustrates a result of image reconstruction performed based on 2D projection images acquired during 2 cardiac cycles. When FIGS. 13A and 13B are compared, it may be confirmed that portions not displayed in the image of FIG. 13A are displayed in the image of FIG. 13B (with reference to portions represented by arrows).

Figure 14A:
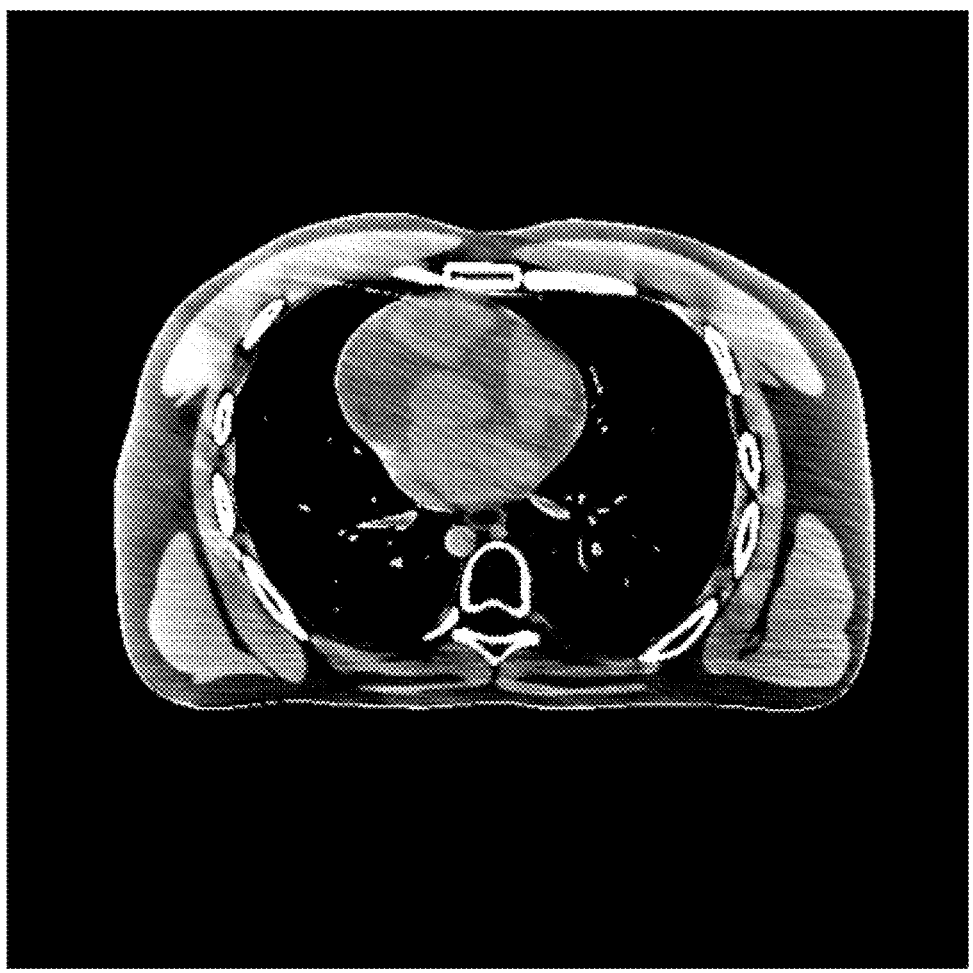
FIG. 14A is a view exemplarily illustrating a result of image reconstruction performed based on 2D projection images acquired during 1 cardiac cycle.
Figure 14B:
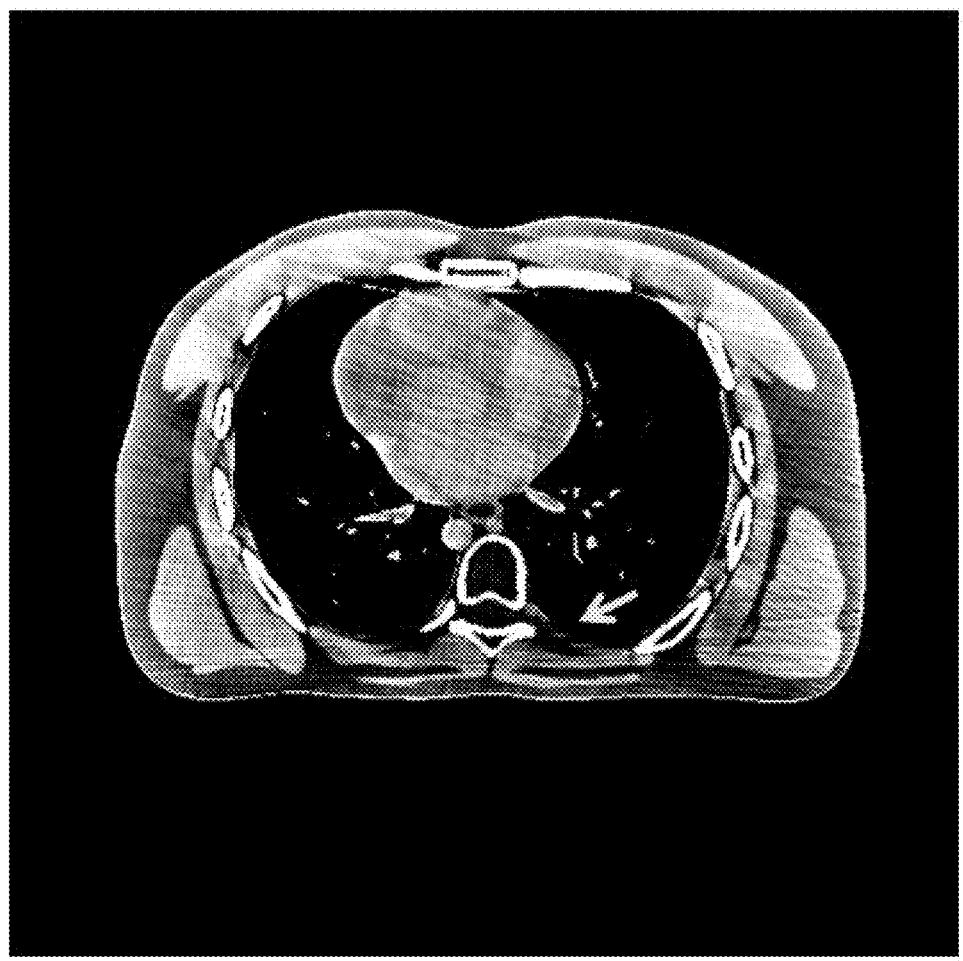
FIG. 14B is a view exemplarily illustrating a result of image reconstruction performed based on 2D projection images acquired during 2 cardiac cycles.

FIGS. 14A and 14B are views exemplarily illustrating results of image reconstruction of the cardiac phase when the heart is contracted by 62%. With reference to FIG. 10, the cardiac phase when the heart is contracted by 62% corresponds to the second section 12 of the cardiac cycle. Therefore, when image construction in the corresponding cardiac phase is performed, the first prior image of FIG. 12 is used.

FIG. 14A exemplarily illustrates a result of image reconstruction performed based on 2D projection images acquired during 1 cardiac cycle. FIG. 14B exemplarily illustrates a result of image reconstruction performed based on 2D projection images acquired during 2 cardiac cycles. When FIGS. 14A and 14B are compared, it may be confirmed that portions not displayed in the image of FIG. 14A are displayed in the image of FIG. 14B (with reference to portions represented by arrows).

Exemplary embodiments have been described above. In the above-described exemplary embodiments, some of the constituent elements of the X-ray imaging apparatus 100 may be implemented as a kind of module.

Here, "module" may refer to a software-based component or a hardware component, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components, such as software components, object-oriented software components, class components, and task components, processes, functions, attributes, procedures, subroutines, segments of program codes, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more CPUs in a device.

In addition to the above-described exemplary embodiments, exemplary embodiments may be implemented through a medium including computer readable codes/instructions to control at least one processing element of the above-described exemplary embodiment, for example, a computer readable medium. Such a medium may correspond to a medium/media which may store and/or transmit the computer readable codes.

The computer readable codes may be not only recorded in a medium but also transmitted over the Internet. For example, the medium may include a magnetic storage medium (for example, a ROM, a floppy disk, or a hard disk), an optical recording medium (for example, a CD-ROM or a DVD), or a transmission medium such as a carrier wave. Further, the medium may be a non-transitory computer readable medium. Since the medium may be a distributed network, the computer readable code may be stored, transmitted and executed in a distributed manner. Further, for example, the processing element may include a processor or a computer processor, and be distributed and/or included in one device.

As is apparent from the above description, in an X-ray imaging apparatus and a control method thereof in accordance with exemplary embodiments, a plurality of 2D projection images is acquired in each cardiac phase by rotating a gantry two times during 2 cardiac cycles and the position of an X-ray generator is adjusted so that X-rays may be radiated from different positions in the same cardiac phase of the respective cardiac cycles, thus enhancing the quality of a 4D image reconstructed from the 2D projection images, even if 2D projection images during a larger number of cardiac cycles are not acquired.

Further, an X-ray dose applied to a patient or medical staff may be reduced simply by adjusting an X-ray dose in the remaining cardiac phases except for specific cardiac phases of the cardiac cycle.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray imaging apparatus comprising:
    an X-ray generator configured to transmit X-ray s to an object;
    an X-ray detector configured to detect the X-ray s transmitted through the object and convert the detected X-ray s into electrical signals;
    a gantry in which the X-ray generator and the X-ray detector are installed so as to be opposite to each other, the gantry being rotatable about a bore;
    a controller configured to control a rotation of the gantry during bio-signal cycles of the object so that the gantry is rotated from different start positions whenever one of the bio-signal cycles is started; and
    an image processor configured to generate a 4D image of the object by applying a prior image-based compressed sensing image reconstruction algorithm to a plurality of 2D projection images acquired from the electrical signals generated by converting the X-ray s detected during the rotation of the gantry,
    wherein the controller controls the gantry to be rotated from a first start position to a second start position during a first bio-signal cycle among the bio-signal cycles and to be rotated from the second start position during a second bio-signal cycle which is continuous with the first bio-signal cycle among the bio-signal cycles,
    wherein the controller controls the gantry to be rotated from the first start position to the second start position during a first bio-signal cycle by rotating the gantry more than 360 degrees,
    wherein the controller is further configured to control a tube current of the X-ray generator so that X-rays of a dose less than a reference dose are applied in phases of the bio-signal cycles of the object except for a first phase and a second phase,
    wherein the first phase is a phase when the object is maximally contracted within the bio-signal cycles, and
    wherein the second phase is a phase when the object is maximally relaxed within the bio-signal cycles.

2. The X-ray imaging apparatus according to claim 1, wherein the controller is configured to rotate the gantry during 2 bio-signal cycles.

3. The X-ray imaging apparatus according to claim 1, wherein a central angle between two of the start positions is within 180 degrees of each other.

4. The X-ray imaging apparatus according to claim 1, wherein the image processor comprises:
    a prior image generator configured to generate prior images by performing image reconstruction of 2D projection images selected according to a designated reference from among the plurality of 2D projection images; and
    an image reconstructor configured to group the plurality of 2D projection images into 2D projection images acquired in the same phases and then perform image reconstruction according to the phases.

5. The X-ray imaging apparatus according to claim 4, wherein the prior image generator is configured to generate a first prior image by performing image reconstruction of 2D projection images acquired within a designated scan range based on a point corresponding to the first phase among an overall scan range of the X-ray generator; and generate a second prior image by performing image reconstruction of 2D projection images acquired within a designated scan range based on a point corresponding to the second phase among the overall scan range of the X-ray generator.

6. The X-ray imaging apparatus according to claim 5, wherein the prior image generator is configured to perform image reconstruction of 2D projection images acquired within the designated scan range among 2D projection images acquired during the first bio-signal cycle.

7. The X-ray imaging apparatus according to claim 5, wherein the prior image generator is configured to perform image reconstruction of 2D projection images acquired within the designated scan range among 2D projection images acquired during the first bio-signal cycle and 2D projection images acquired within the designated scan range among 2D projection images acquired during the second bio-signal cycle.

8. The X-ray imaging apparatus according to claim 5, wherein the image reconstructor is configured to perform image reconstruction using at least one of the first prior image and the second prior image according to a phase in which image reconstruction will be performed, when image reconstruction is performed according to the phases.

9. A control method of an X-ray imaging apparatus comprising:
    controlling a rotation of a gantry, in which an X-ray generator and an X-ray detector are provided so as to be opposite to each other, during bio-signal cycles of an object so that the gantry is rotated from different start positions whenever the bio-signal cycles are started; and
    generating a 4D image of the object by applying a prior image-based compressed sensing image reconstruction algorithm to a plurality of 2D projection images of the object acquired during the rotation of the gantry,
    wherein the controlling the rotation of the gantry comprises controlling the gantry to be rotated from a first start position to a second start position during a first bio-signal cycle among the bio-signal cycles and to be rotated from the second start position during a second bio-signal cycle which is continuous with the first bio-signal cycle among the bio-signal cycles,
    wherein the controlling the rotation of the gantry further comprises rotating the gantry from the first start position to the second start position during a first bio-signal cycle by rotating the gantry more than 360 degrees, wherein the control method further comprises controlling a tube current of the X-ray generator so that X-rays of a dose less than a reference dose are applied in phases of the bio-signal cycles of the object except for a first phase and a second phase, wherein the first phase is a phase when the object is maximally contracted within the bio-signal cycles, and wherein the second phase is a phase when the object is maximally relaxed within the bio-signal cycles.

10. The control method according to claim 9, wherein the controlling of the rotation of the gantry includes controlling the rotation of the gantry during 2 bio-signal cycles.

11. The control method according to claim 9, wherein, during the controlling of the rotation of the gantry, a central angle between two of the start positions is within 180 degrees of each other.

* * * * *